US00PP13008P2

(12) United States Plant Patent
Walsh

(10) Patent No.: US PP13,008 P2
(45) Date of Patent: Sep. 24, 2002

(54) *MISCANTHUS SINENSIS* PLANT NAMED 'LITTLE ZEBRA'

(75) Inventor: Thomas M. Walsh, Nunica, MI (US)

(73) Assignee: Hortech, Inc., Spring Lake, MI (US)

( * ) Notice: Subject to any disclaimer, the term of this patent is extended or adjusted under 35 U.S.C. 154(b) by 11 days.

(21) Appl. No.: 09/765,699

(22) Filed: Mar. 19, 2001

(51) Int. Cl.[7] ..... A01H 5/00
(52) U.S. Cl. ..... Plt./384
(58) Field of Search ..... Plt./384

*Primary Examiner*—Bruce R. Campell
*Assistant Examiner*—Annette H. Para

(57) ABSTRACT

A Japanese silver grass named 'Little Zebra', characterized by its narrow, green and yellow banded foliage, dwarf habit, and silvery white late-summerborne flowers.

6 Drawing Sheets

FEDERALLY SPONSORED RESEARCH

This application does not relate to any federally sponsored research.

CROSS REFERENCE

This application does not cross reference with other related applications.

BACKGROUND OF INVENTION

'Little Zebra' originated as a bud sport (mutation) from the species *Miscanthus sinensis* and is similar to the parent species only in the habit (shape) of the plant. The first successful asexual reproduction of 'Little Zebra' was carried out by its discoverer, Thomas M. Walsh. This propagation took place under controlled conditions in Nunica, Mich., on Aug. 1, 1995.

The mutated bud was divided (with a section of crown, foliage, and roots from the parent plant) and potted in an organic growing medium. This division survived and was transplanted to an outdoor growing bed where it was grown to mature size.

SUMMARY OF INVENTION

Once rooted, the variegated sport was planted out in the landscape where it displayed narrow green and yellow striped leaves, dwarf habit (in relation to the parent species), and late summertime bloom time.

DESCRIPTION OF THE VARIOUS VIEWS OF THE DRAWINGS

The accompanying photographic figures show typical foliage and growth habit of the cultivar and the closest known comparison plants (*Miscanthus sinensis* ) 'Hinjo' (a.k.a. 'Little Nicky'), *Miscanthus sinernsis*'Puntchen', and *Miscanthus sinensis* 'Zwergzebra' with color being as accurate as possible with renditions of this type. The photographs were taken at 11 A.M. on Sep. 10th 2000 under cloudy conditions, in Nunica, Mich. The film used was Kodak Gold ISO 200 exposed for 1/30 second at F 5.6 using no filters.

DETAILED BOTANICAL DESCRIPTION

Figure 1:
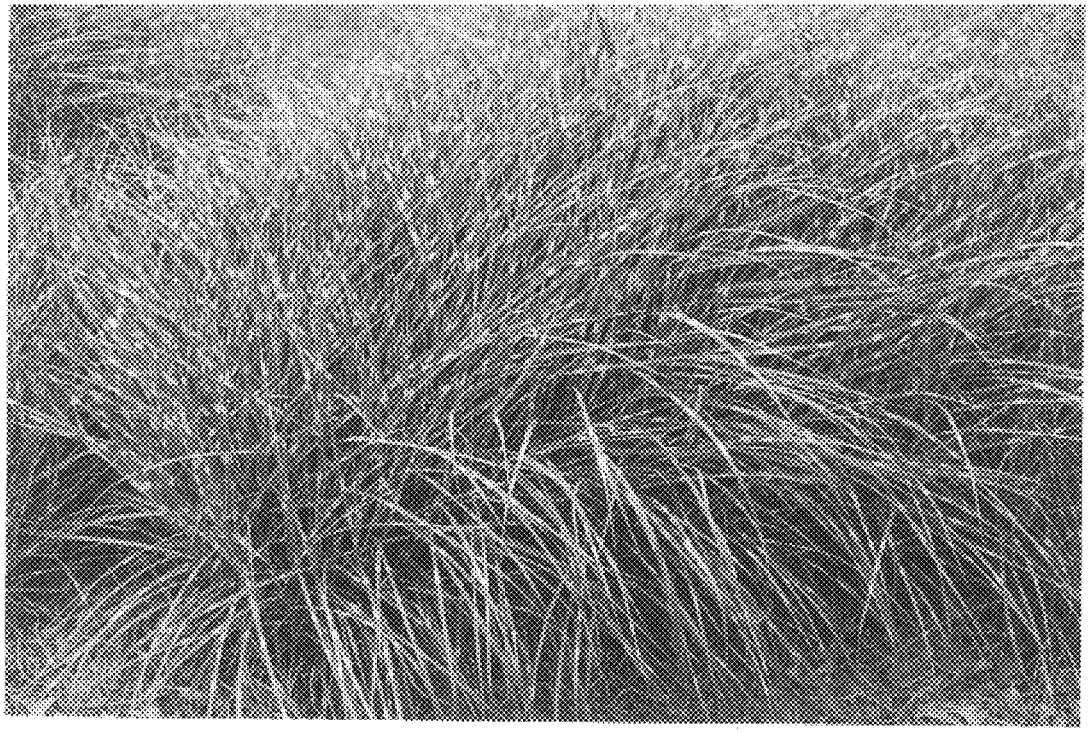
FIGS. 1–3 are perspective views of *Miscanthus sinensis* 'Little Zebra'.
Figure 2:
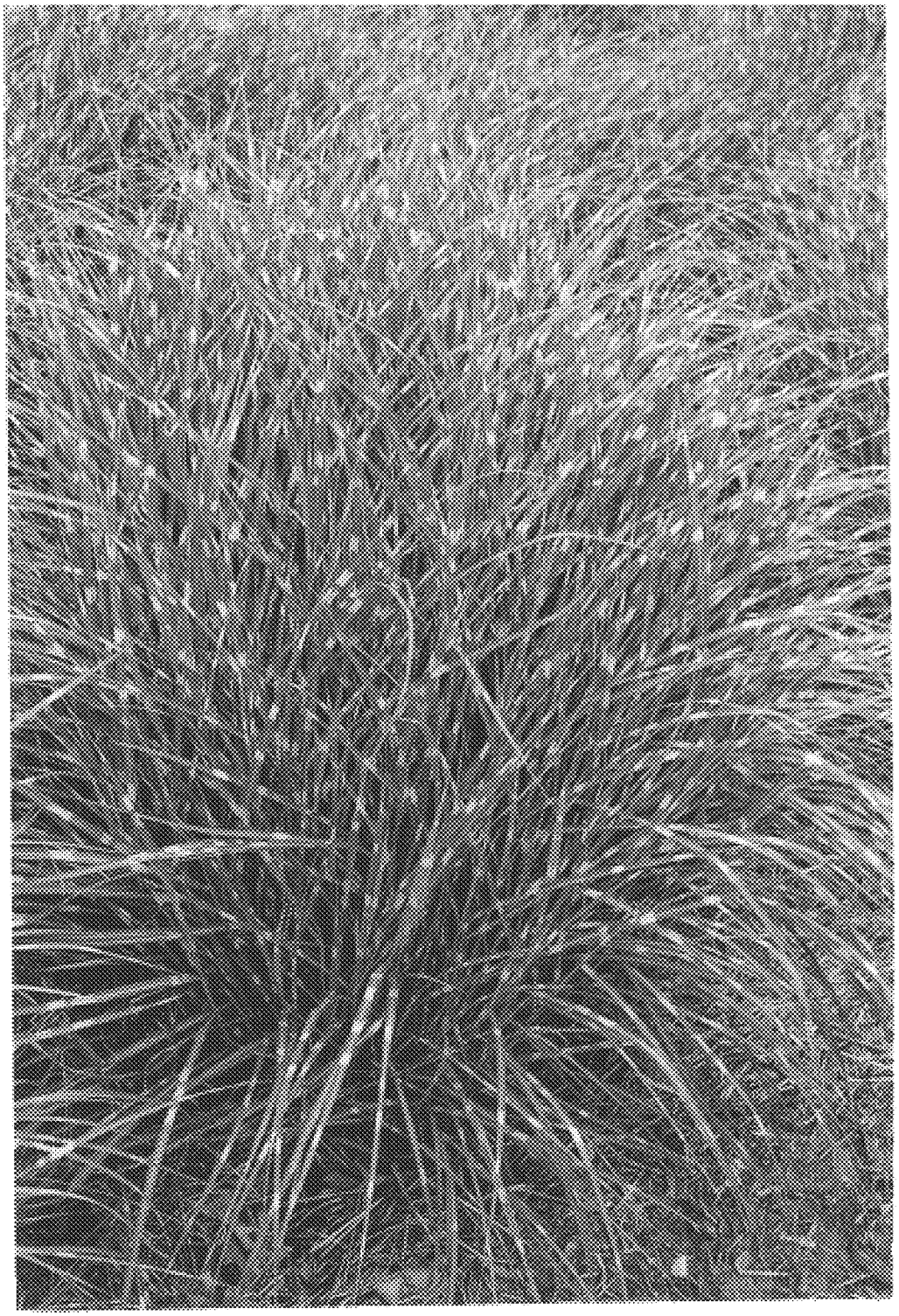
Figure 3:
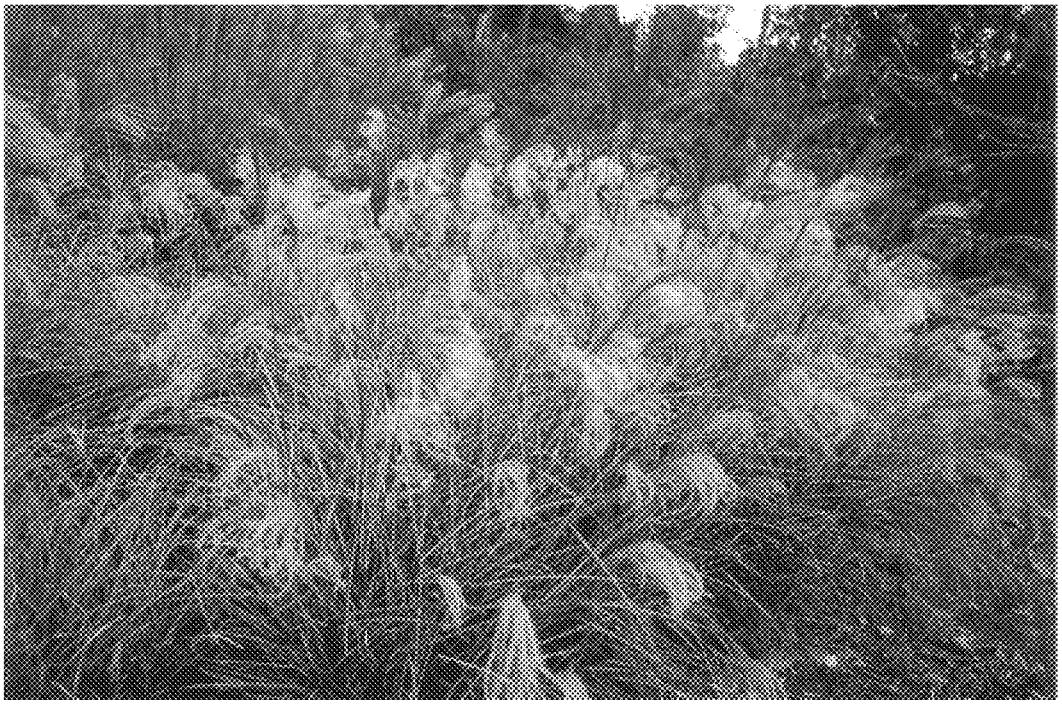
Figure 4:
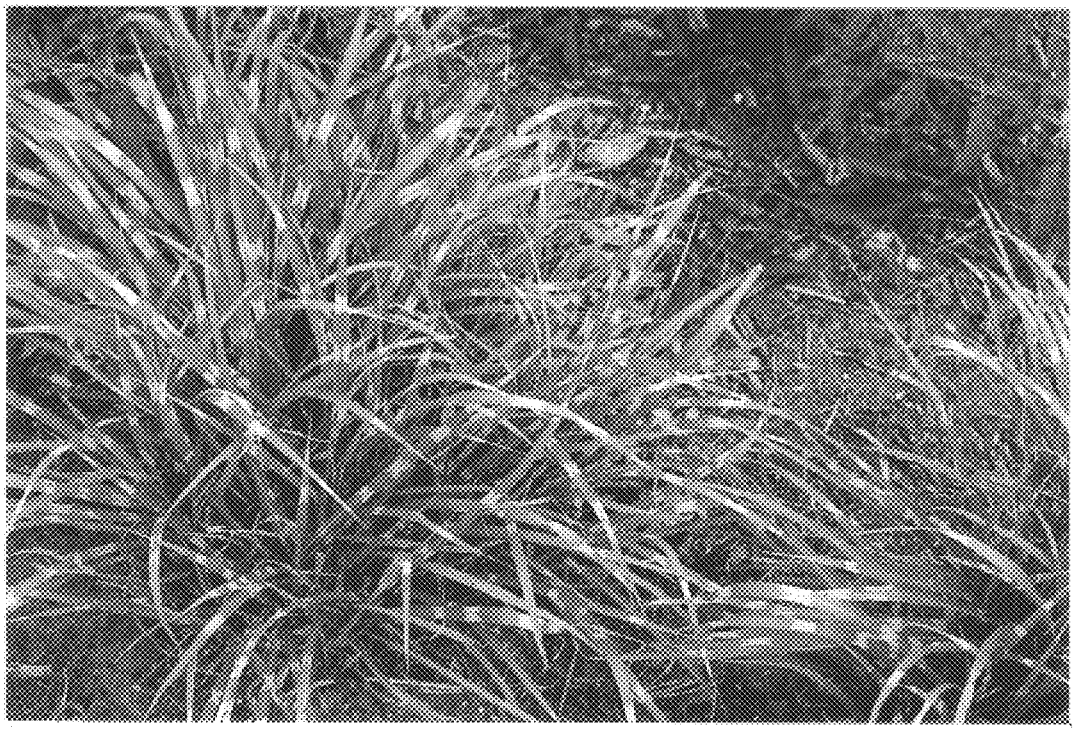
FIG.4 (prior art)
FIGS. 4 is a perspective view of *Miscanthus sinensis* 'Hinjo'.
Figure 5:
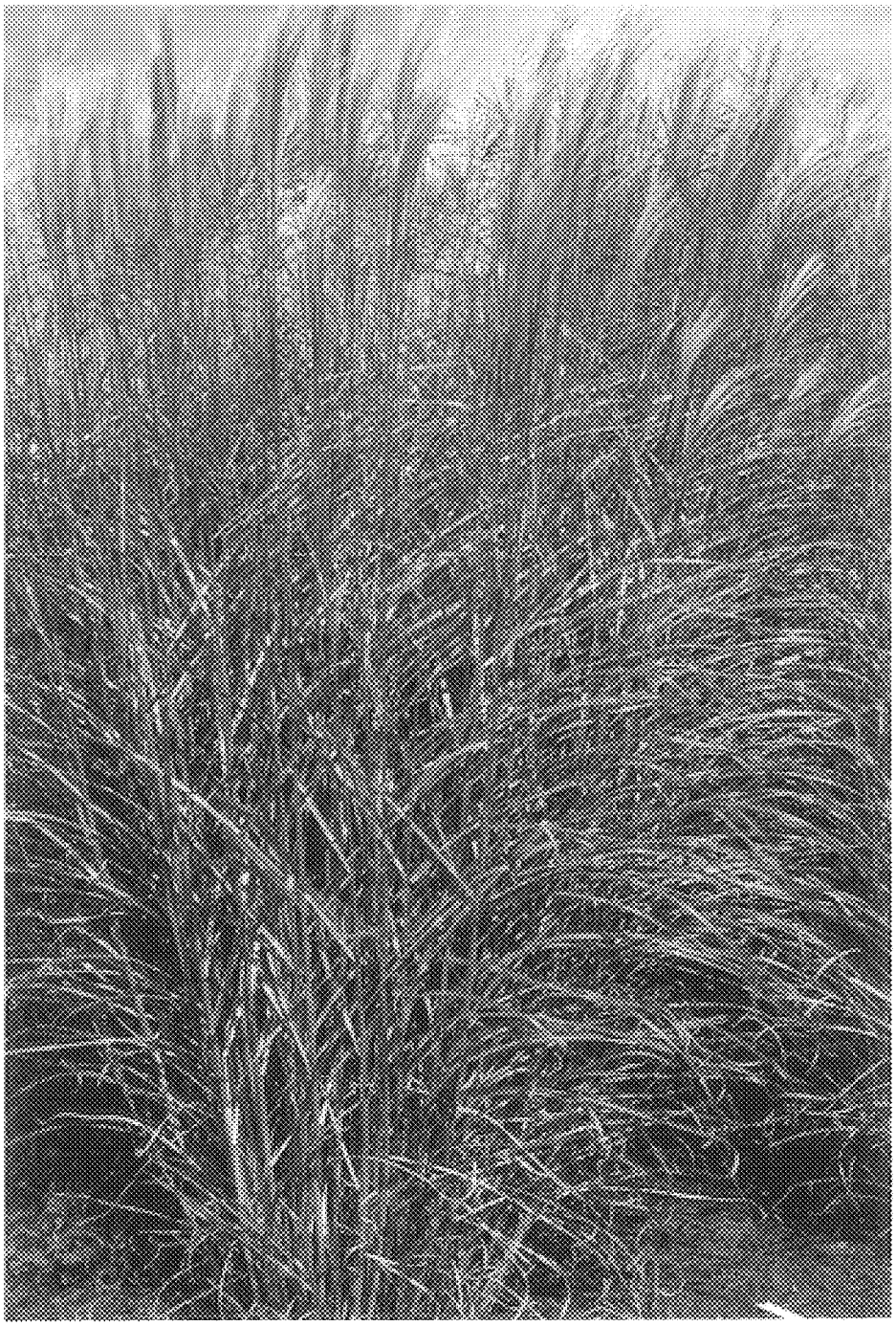
FIG. 5 is a perspective view of *Miscanthus sinensis* 'Puenktchen'.
Figure 6:
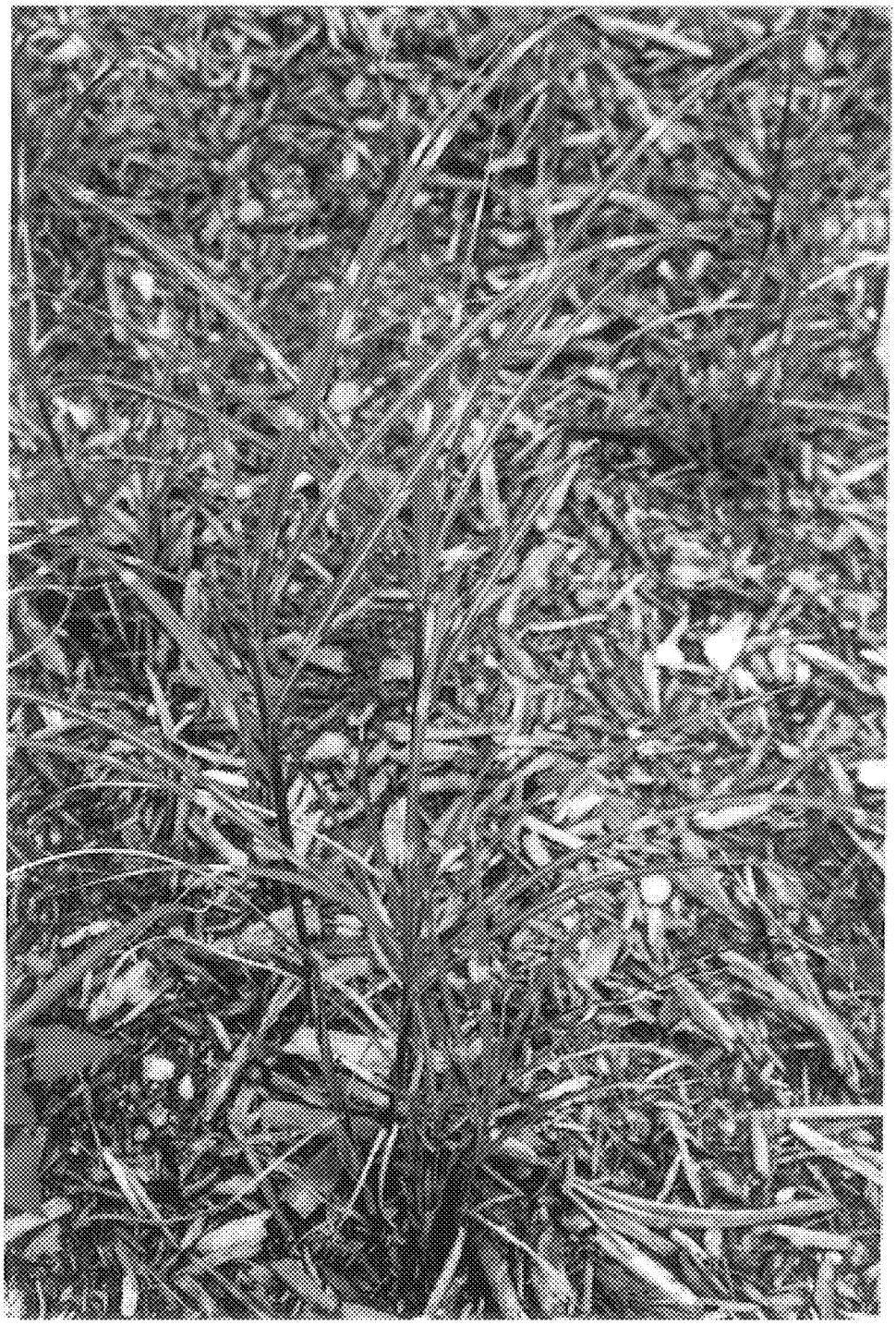
FIG.6 (prior art)
FIG. 6 is a perspective view of *Miscanthus sinensis* 'Zwergzebra'.

'Little Zebra' has not been observed under all possible environmental conditions, and the phenotype may vary significantly with variations in environment; such as temperature light intensity and day length. The following observations, measurements, and comparisons describe this plant as grown in Nunica, Mich. when grown outdoors without cover.

The following traits have been repeatedly observed and are determined to be basic characteristics of 'Little Zebra' which in combination distinguish this Japanese silver grass as a new and distinct cultivar. The color codes correspond to The Royal Horticultural Society Colour Chart. The following description is based upon a three year old plant that is mature in every respect.

1. Deciduous foliage is linear, alternate, crowded at the base of the plant. Each is attached to a cylindrical, pith-filled, jointed culm (stem), 1/8 to 3/16 inch wide, colored green 134-A. The culms in the center of each clump are held erect. Those farther out tend to arch away from the center of the plant, on as much as a 15 degree angle. The distance between the leaves ranges from 1/4 inch at the base of the culm increasing to 5 inches toward the end of the culm.

2. Flattened mostly basal leaf blades are attached to the culm at their ligules which are colored green 134-A. Each ligule is hairless and encircles the culm 1/2 way around. Auricles are absent. Leaf blades range from 10 to 13 inches long, 3/16 to 1/4 wide, and are finely bristle haired along their edges, except for about 1 inch at the base of the blade which is smooth edged. Leaf blades gradually taper to a slender pointed tip and are oriented on an acute angle of approximately 30 degrees in relation to the distal end of the culm.

3. Each leaf blade is colored with alternating horizontal bands of yellow and green which extend from one edge of the leaf to the other; the green bands, green 134-A, range from 1 to 3 inches in height. The yellow bands, yellow 8-C, range from 3/8 to 1 inch in height.

4. Each leaf blade has a central prominent longitudinal midrib, 1/8 inch wide, color green 134-D. The overall veination pattern is longitudinal/parallel with the thin (less than 1/32 inch wide) veins being relatively unnoticable, and colored the same as the corresponding surrounding leaf tissue.

5. Below each ligule is a sheath that ranges from 1/4 inch in length, at the base of the culm, to 5 inches in length, at the very top of the culm. Each leaf sheath originates at a slightly swollen node, colored green 134-B, and ranging from 3/16 to 1/4 inch wide. The sheaths fully encircle the culm from the node to about 1/3 way up to the ligule, the top 2/3 of the sheath encircles about 1/2 way round the culm.

6. Each culm ultimately terminates in a late summerborne corymbose panicle (inflorescence) of 10 to 13 racemes: each raceme to 6 inches long, axis of the panicles shorter than or about as long as the racemes. The tiny bisexual flowers (spikelets) are grayed purple in youth, 184-C, maturing to grayed yellow 161-D.

7. Flowers are paired, 1/8 inch long, with protruding silky silvery white, 155-D, hairlike unbranched stigmas. The 1/6 inch long cigar-shaped anthers are carried upon hair-thin filaments and bear yellow-orange, 14-B, pollen, The flowers are not fragrant.

8. No seed formation has been observed in Michigan but farther south, where the growing season is longer, one would expect to see tiny grain formed.

9. The general growth habit of 'Little Zebra' is dense-clump forming. Clumps have been observed to measure 1½ feet across at ground level after four years. The mode of expansion is short rhizomes.

Other cultivars of *Miscanthus sinensis* include 'Hinjo' which is not patented. 'Hinjo' is taller than 'Little Zebra', reaching 4 feet tall. It blooms much more sparsely than 'Little Zebra', and it differs also in having wider leaves and leaves that are frequently discolored with red blotches caused by the fungus Helmenthosporium. 'Puenktchen', is not patented and is much taller than 'Little Zebra', being 5 to 7 feet tall. It is wider leaved, and it differs in that its leaves are green and yellow banded in spring then turn all-green during the course of the growing season. The foliage of 'Little Zebra' does not turn green throughout the growing season, but retains its yellow and green banded coloration. Finally, the cultivar 'Zwergzebra', is not patented, and differs from 'Little Zebra' by being much taller, 5 to 6 feet tall, with broader foliage. Additionally, in respect to 'Little Zebra', its leaves have far fewer yellow bands, and it differs in having culm bases of reddish purple instead of green.

Propagation is successfully achieved year-round by crown division, and during the growing season by leaf and node cuttings. Plants produced by these methods remain true to type. No resistance or unusual susceptibility to common diseases and pest of this host has, to date, been observed or verified.

I claim:

1. A new and distinct Japanese silver grass plant named *Little Zebra*, as described and illustrated.

* * * * *

FIG.5(priorart)